United States Patent [19]

Howes

[11] 4,451,624
[45] May 29, 1984

[54] POLYMERS, PREPARATION AND USE

[75] Inventor: John G. B. Howes, Hertford Heath, England

[73] Assignee: Smith and Nephew Associated Companies Ltd., England

[21] Appl. No.: 330,013

[22] Filed: Dec. 11, 1981

[30] Foreign Application Priority Data

Dec. 12, 1980 [GB] United Kingdom ............ 8039934

[51] Int. Cl.$^3$ ............................................. C08F 210/00
[52] U.S. Cl. ............................. 526/292.2; 424/78; 525/326.7; 526/287; 526/312
[58] Field of Search ............... 526/258, 287, 292.2, 526/312; 525/326.7

[56] References Cited

U.S. PATENT DOCUMENTS

| | | | |
|---|---|---|---|
| 3,515,707 | 6/1970 | Reimschuessel et al. | 525/328.3 |
| 3,539,684 | 11/1970 | Hoover | 424/78 |
| 3,551,384 | 12/1970 | Zelt | 526/258 |
| 3,840,504 | 10/1974 | Keim | 526/258 |
| 3,912,693 | 10/1975 | Shimizo et al. | 526/292.2 |
| 4,026,945 | 5/1977 | Green et al. | 526/258 |
| 4,304,894 | 12/1981 | Andrews | 526/310 |

Primary Examiner—Harry Wong, Jr.
Attorney, Agent, or Firm—Jacobs & Jacobs

[57] ABSTRACT

Polymers containing 55 to 90% of units of the formula (A):

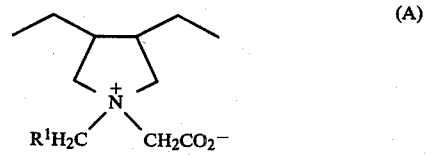

(A)

wherein $R^1$ is a hydrogen atom or an alkyl group of 1 to 3 carbon atoms; and 10 to 45% of units of the formula (B) and (C):

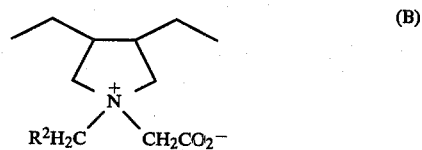

(B)

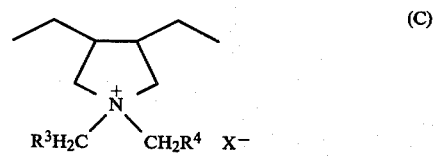

(C)

wherein $R^2$ is a hydrogen group of 5 to 19 carbon atoms, for example n-$C_{11}H_{23}$, $R^3$ is a hydrogen atom or an alkyl group of 1 to 3 carbon atoms, $R^4$ is a hydrocarbon group of 5 to 19 carbon atoms, for example n-$C_{11}H_{23}$ and $X^-$ is an anion and which contain at least 10% of units of formula (C) and are free from polymeric species having a molecular weight of less than 10,000 are described. The polymers possess antimicrobial activity agains common pathogens. Isotonic aqueous solutions containing 0.002 to 0.025% of the polymer are suitable for the sterilization of contact lenses for example by immersion of the lens in the solution overnight. Hydrophilic ointments containing from 0.002 to 0.25% of the polymer are suitable for the treatment of bacterial infection of lesions of the skin such as burns and ulcers.

8 Claims, No Drawings

POLYMERS, PREPARATION AND USE

This invention relates to a novel class of heterocyclic polymers possessing quaternary ammonium groups, to their preparation and to their use as antimicrobial agents.

Homopolymers of the type based on units of formula (I):

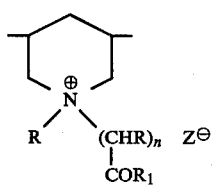

wherein R is hydrogen or an alkyl group of up to 18 carbon atoms; and $R_1$ is halogen or —OH, —NHOH, —NHNH$_2$, —NH$_2$ or —NHR where R is defined above; $Z^{\ominus}$ is an anion; and n is an integer from 1 to 20; are described in British Patent Specification No. 1,178,371 and U.S. Pat. No. 3,515,707. These homopolymers are used to form metal chelate complexes which are cast into films and used as semiconductors. No suggestion was made that these polymers possess any bactericidal properties.

British Patent Application No. 2027040A describes inter alia terpolymers based on various units of formula (II):

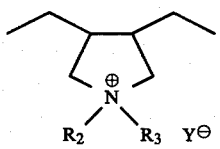

wherein $R_2$ is most aptly methyl, $R_3$ is most aptly methyl, n-octyl or n-dodecyl and $Y^{\ominus}$ is an anion compatible with water solubility of the polymer. These compounds were said to be useful inter alia for the sterilisation of soft contact lenses. Unfortunately it has been found that these known terpolymers when used to sterilise soft contact lenses can increase the amount of protein deposited thereon in normal use. This is a disadvantage in that it can lead to the necessity of very frequent deproteinisation operations. Clearly it would be desirable to provide material that would show less propensity to cause protein deposition coupled with acceptable antimicrobial efficiency so that it could be more readily used for a range of purposes including most importantly the sterilisation of soft contact lenses. Such materials have now been discovered.

Accordingly the present invention provides a polymer which consists essentially of 55 to 90% by weight of units of formula (A):

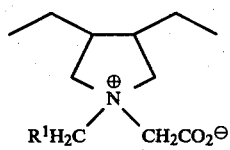

wherein $R^1$ is a hydrogen atom or an alkyl group of 1 to 3 carbon atoms; and 10 to 45% by weight of units of formula (B) and (C):

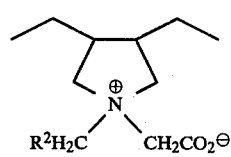

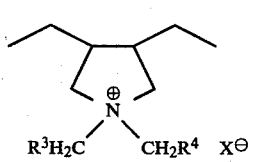

wherein $R^2$ is a hydrocarbon group of 5 to 19 carbon atoms; $R^3$ is a hydrogen atom or an alkyl group of 1 to 3 carbon atoms, $R^4$ is a hydrocarbon group of 5 to 19 carbon atoms and $X^{\ominus}$ is an anion.

When used herein % are on a wt./wt. basis unless otherwise stated.

Whilst the polymers of the present invention consist essentially of units of formula (A), (B), and (C) as hereinbefore described up to 10% of the polymer may comprise of one or more compatible monomers capable of copolymerisation with units of formula (A), (B) and (C). Generally not more than 5% and preferably not more than 2% of such other units are included. Most preferably no such other units are included.

It is preferred that $R^1$ is a hydrogen atom.

Suitable groups $R^2$ include alkyl groups and especially those in which the alkyl group is an n-alkyl group. Favourably the group $R^2$ contains from 7 to 13 carbon atoms. A preferred group for $R^2$ is the n-$C_{11}H_{23}$ group.

It is preferred that $R^3$ is a hydrogen atom.

Suitable groups $R^4$ include alkyl groups and especially those in which the alkyl group is an n-alkyl group. Favourably the group $R^4$ contains from 7 to 13 carbon atoms. A preferred group for $R^4$ is the n-$C_{11}H_{23}$ group.

Suitable anions $X^{\ominus}$ include chloride, bromide, iodide, sulphate, acetate, gluconate and the like. Generally the anion is chosen to impart a water solubility of at least 0.1% and preferably at least 0.5% w/v at 20° C. The anion is naturally a nontoxic anion and is preferably suitable for instillation into the eye.

Preferably $X^{\ominus}$ is $Cl^{\ominus}$.

Favourably the content of units of the formula (A) in the polymer is from 60 to 80%, more suitably is from 62 to 70% and preferably is 65%.

Suitably the contents of units of the formula (B) in the polymer is up to 22%, more suitably is 15 to 20% and preferably is 17.5%.

Suitably the content of units of the formula (C) in the polymer is from 10 to 35%, more suitably is from 15 to 30% and preferably is 17.5%.

The combined weight of units of the formulae (B) and (C) in the polymer of this invention is favourably from 20 to 40%. To ensure best bactericidal effectiveness at least 10% of the weight of the polymer should be present as units of formula (C).

A preferred polymer consists of 65% units of the formula (A), 17.5% of units of the formula (B) and 17.5% of units of the formula (C). Such polymer is especially preferred when $R^1$ and $R^3$ are hydrogen atoms and $R^2$ and $R^4$ are n-$C_{11}H_{23}$ groups and $X^{\ominus}$ is a chloride anion. Such a polymer is believed to posses particularly advantageous properties with regard to bactericidal effectiveness and low protein deposition on contact lenses.

A further aspect of the present invention comprises a process for the preparation of the polymers of the invention by de-esterification of an ester of a salt of the polymer of the invention followed by isolation of the polymer of the invention.

Suitably the ester of the polymer is an alkyl ester in which the alkyl group contains 1 to 4 carbon atoms. Preferably the ester is the methyl ester.

Suitably the salt of the polymer is a salt having the anion $X^{\ominus}$ as described above. Preferably the anion $X^{63}$ is $Cl^{\ominus}$.

Suitably the de-esterification of the ester is carried out in an aqueous solution at acid, neutral or alkaline pH values. Preferably the de-esterification is carried out in the presence of a mineral acid, such as sulphuric, hydrochloric or nitric acid and the like. A particularly preferred mineral acid is hydrochloric acid.

Suitably the de-esterification is carried out at an elevated temperature, most aptly the temperature is from 80° to 100° C. and is preferably from 96° to 98° C.

Suitably the polymer of the invention is isolated after the de-esterification reaction by de-acidifying the product of the de-esterification reaction. This may be carried out by chemical means, such as precipitation of the anion $X^{\ominus}$ as insoluble metallic salt followed by neutralisation of the acid by a suitable base such as an aqueous solution of an alkali metal hydroxide or ammonia or by physical means such as passing through an ion exchange resin to remove the anion $X^{\ominus}$ or by dialysing through a semi-permeable membrane.

It is preferred to isolate the polymer of the invention by de-acidification by dialysis using cellulose acetate tubing.

Most suitably the polymer of this invention is free from low molecular weight materials, for example is free of material of weight less than 10,000 and preferably less than 15,000. (Molecular weights are expressed on wt. average basis).

In another favourable process for the de-esterification of the ester which avoids the use of an elevated temperature the process is carried out in an aqueous solution having an alkaline pH value. Suitably after the polymerisation of the monomers to form the ester of the salt of the polymer, the viscous oil obtained is diluted with water and an aqueous solution of an alkali metal hydroxide or ammonia is added and the alkaline solution allowed to stand for a period sufficient for de-esterification to be complete, for example 1 to 4 hours, at ambient temperature, that is 15° to 25° C. Preferably the alkali metal hydroxide used is sodium hydroxide. After completion of the de-esterification reaction the pH value of the solution is adjusted to pH 7 by addition of an aqueous solution of a mineral acid as defined above. A preferred mineral acid is hydrochloric acid. The neutral solution is then dialysed using cellulose acetate tubing as described above for a period of up to 21 days, preferably 7 to 16 days, for example 14 days.

A further aspect of this invention comprises a pharmaceutical composition containing an antimicrobially effective amount of a polymer of the invention hereinbefore described together with a pharmaceutically acceptable carrier.

The antimicrobially effective amount present in the compositions of this invention will normally be 0.001 to 0.5%, will suitably be 0.002 to 0.25%, more suitably be 0.005 to 0.1% and preferably will be 0.01 to 0.05%. The higher concentrations (for example greater than or equal to 0.1% will generally be suitable for skin antisepsis or the like whereas lower concentrations (less than 0.1% and preferably less than 0.05% may be employed in the sterilisation of soft contact lenses).

Suitable pharmaceutically acceptable carriers will include liquids, ointments, lotions, pastes, emulsions, aqueous gels, oily suspensions, water soluble polymeric films, water-insoluble films capable of sustained release of the antimicrobial agent and the like. The preferred carriers will be aqueous solutions suitable for soft lens sterilisation.

It is preferred that pharmaceutical compositions of the present invention are substantially free of ionic materials. The inclusion of ionic material such as sodium chloride and the like may cause reduction in the activity of the polymers of the present invention.

The pharmaceutical composition of this invention is preferably sterile. Liquid compositions are most easily prepared and sterilised by dissolving an appropriate amount of polymer of this invention in the liquid and filtering through an 0.22 micron cellulose ester filtration membrane (available from Millepore Corp., Bedford, Mass.) into the appropriate sterile package presentation. A preferred liquid composition comprises a sterile aqueous solution.

Another pharmaceutical composition particularly suitable for topical application is a sterile ointment. This will conveniently have a hydrophilic ointment base such as an oil-in-water emulsion.

Suitable ointment bases are described in Chapter 87 in Remingtons Pharmaceutical Sciences, 15th Edn. 1975 pages 1532-4 and in U.K. Patent Specification No. 1,240,545. The ointments are conveniently made by mixing together under aseptic conditions the pre-sterilised components at elevated temperature and allowing to cool before filling into the appropriate packaging. Suitably the ointment may also contain an additional antimicrobial agent such as silver sulphadiazine or a chlorhexidine salt. Preferred chlorhexidine salts are those of gluconic or acetic acid.

The present invention also provides a method of treating diseases of the skin or other mucous membranes arising from bacterial infection or lesions of the skin such as burns or ulcers which comprises applying thereto a pharmaceutical composition (especially an ointment) of this invention.

A further aspect of this invention provides an aqueous solution containing an antimicrobially effective amount of the polymer adapted to use in the sterilisation of a surface. The aqueous solution is preferably adapted for the sterilisation of a contact lens and most preferably adapted for the sterilisation of a soft contact lens.

Normally an aqueous solution for this aspect of the invention will contain 0.001 to 0.1% of a polymer of this invention, suitably from 0.002 to 0.06%, more suitably from 0.005 to 0.05% of a polymer of this invention and preferably will contain 0.02 to 0.03% of a polymer of this invention.

Desirably the aqueous solution of this aspect of the invention will contain a tonicity adjusting agent in an amount suitable to render the solution substantially isotonic with human tears, that is, a tonicity equivalent to an aqueous solution containing from 0.8 to 1.1% of sodium chloride and preferably equivalent to 0.9% sodium chloride. Aptly the tonicity adjusting agents are nonionic agents such as glycerol, polypropylene glycol, dextrose, urea or other non-ionic tonicity agents. The amount of tonicity adjusting agent will differ depending upon the agent used. A list of sodium chloride equivalents is given in Remingtons Pharmaceutical Sciences, 15th Edn. Chapter 79 pages 1408-12. Thus for example, the amount of dextrose present in the solution is suitably from 4.0 to 5.5%, and is most preferably 5%, while the amount of urea present in the solution is suitably from 1.5 to 1.7% and is preferably 1.63% and the amount of glycerol present in the solution is suitably from 2.0 to 3.0% and is preferably 2.5% and the amount of propylene glycol present in the solution is suitably from 1.8 to 2.5% and is preferably 2.0%.

Optionally the aqueous solution may also contain other compatible antimicrobial agents such as thiomersal but in general this is not a preferred feature of the invention. One of the considerable advantages of the use of the present polymers is that, if desired, they allow the avoidance of the use of additional antimicrobial agents.

Optionally the aqueous solution may also contain a buffering system such as disodium hydrogen phosphate and potassium dihydrogen phosphate but in general the polymer will dissolve in water to give a pH value of between 6.5 and 7.5 and the presence of a buffer is not a preferred feature of the invention. The avoidance, if desired, of such buffers is also an advantage of use of the polymers of this invention.

The invention also provides a method of sterilising a contact lens by contacting said lens with an aqueous solution containing an antimicrobially effective amount of a polymer of the invention for sufficient time to sterilise said lens, suitably is from 2 to 10 hours and preferably is from 4 to 8 hours.

Most suitably from 1 to 20 ml of a solution containing an antimicrobially effective amount of a polymer of this invention is employed per lens to be sterilised and preferably from 3 to 12 ml, for example 5 or 10 ml is used.

In the method of the present invention the lens may be contacted with the aqueous solution in a lens case. Suitable lens cases will have a volume of between 1 and 20 ml and more suitably from 3 to 12 ml, for example 10 ml. The lens case may comprise a single chamber for receiving the solution. In such cases a lens holder capable of holding each lens from right or left eye separate from each other is required. Alternatively the lens case may comprise a pair of chambers (one for each lens). It is desirable that which ever type of lens case is used the lens is allowed to float freely in the solution so that the entire surface is wetted by the solution and thereby effectively sterilised. Suitable lens cases will be closed by a bacteria-proof closure so that bacteria are not admitted to the interior of the lens case during the sterilising cycle. The skilled worker will know the type of screw cap or snap top closure which is bacteria-proof.

Containers for compositions of this invention are made from materials which are sterilisable and will not absorb deleterious amounts of polymer from the composition. Suitable materials include low density polyethylene. Containers made from low density polyethylene may be sterilised using ethylene oxide or gamma irradiation and stored until required for filling. Such containers of polyethylene may be filled and stored without the composition unacceptably losing effectiveness through absorption of the polymer from the solution into the walls of the container. Suitable multi-dose containers will have a volume of 25 to 250 ml. Although it is preferred that the volume of the container is 100 to 150 ml, for example about 125 ml to contain solution for 20 to 30 days of daily use. Suitable multi-dose containers may be closed by a screw cap and the solution dispensed through a restricted opening such as a dropper tip. Alternatively, though not desirably, the compositions of the present invention may be filled into unit dose containers, for example sachets capable of containing 10 to 20 ml of solution.

Suitably the method of this invention is applied to the sterilisation of contact lenses, such as soft (that is hydrophilic) contact lenses, silicone-based contact lenses and gas permeable contact lenses. The method is preferably used to sterilise soft contact lenses.

A further aspect of this invention provides an aqueous solution containing an antimicrobially effective amount of the polymer together with a non-ionic surface active agent which solution is adapted for use as a cleaning, sterilising and wetting solution for contact lenses, particularly hard and gas-permeable lenses. Hard and gas-permeable lenses are conventionally manufactured from hydrophobic materials such as polymethylmethacrylate, cellulose acetate butyrate, silicone polymers and copolymers of silicone and acrylate monomers. After sterilisation and removal from the sterilising solution it is desirable that the surfaces of the lenses should be treated with a sterile, isotonic solution of a wetting agent to avoid possible discomfort immediately after replacement of the lens in the eye. Certain wearers of such contact lenses may require instillation of such a solution directly into the eye during the wearing period to avoid discomfort. It has now been found that by employing a non-ionic surface active agent with a polymer of this invention in a substantially isotonic, aqueous solution, a solution favoured for sterilising and wetting hard and gas permeable lenses is provided. It is an advantage of such solutions that the antibacterial properties of the polymer are not impaired by the presence of a non-ionic surface active agent.

Suitably the solutions of this aspect of the invention will contain from 0.001 to 0.1% of the polymer and more suitably 0.0015 to 0.05% and preferably will contain 0.002 to 0.025% of the polymer.

Suitably the solutions of this aspect of the invention will be substantially isotonic as hereinbefore defined. Preferably the tonicity adjusting agent will be a non-ionic tonicity adjusting agent as hereinbefore defined.

Suitable non-ionic surface active agents for inclusion in the solutions of this aspect of the invention include poly(oxyethylene)-poly(oxypropylene) block copolymers (commonly known as Pluronics, trade mark of Wyandotte Corp). Such polymers are formed by the condensation of propylene oxide onto a propyleneglycol nucleus followed by the condensation of ethylene oxide on to both ends of poly(oxypropylene) base. The poly(oxyethylene) groups on the ends of the molecule are controlled in length to constitute from 10 to 80% by weight of the final molecule. Suitable polymers will have a molecular weight of between 1900 to 15,500.

Suitable block copolymers for use in the invention include the following Pluronic copolymers, Pluronic L62 (molecular weight 2100, % polyoxyethylene 20%), Pluronic L64 (2900, 40%), Pluronic F68 (8350, 80%), Pluronic F108 (15,500, 80%) and Pluronic F127 (11,500, 70%). A preferred block copolymer is the polymer having a molecular weight of 2900 and containing 40% polyoxyethylene in the total molecule, known as Pluronic L64.

Suitably the solutions of the present invention will contain 0.01 to 2.5% of the non-ionic surface active agent based on the weight of the composition. More suitably the solutions will contain 0.05 to 1.5% and preferably 0.1 to 1% for example 0.5%.

From the foregoing it will be appreciated that in a preferred aspect this invention provides an aqueous isotonic solution suitable for the sterilisation and wetting of contact lenses which comprises a sterile, isotonic, aqueous solution of from 0.001 to 0.1% of a polymer of the present invention, from 0.01 to 2.5% of a non-ionic surface active agent rendered isotonic with a non-ionic tonicity adjusting agent.

In a particularly preferred aspect this invention provides an aqueous isotonic solution suitable for the sterilisation and wetting of contact lenses which comprises a sterile isotonic aqueous solution of from 0.002 to 0.025% of a polymer of the present invention, from 0.1 to 1.0% of a poly(oxyethylene)-poly(oxypropylene) block copolymer having a molecular weight between 2100 and 15,500, rendered isotonic with a non-ionic tonicity adjusting agent.

Prepolymers for units of formula (A) and (B) may be prepared by condensing an N-alkyl substituted diallyl amine with a halocarboxylic ester in an inert solvent (see for example U.S. Pat. No. 3515707). Alternatively a N,N-diallyl-glycinate may be reacted with an alkyl halide such as octyl bromide in a solvent such as a lower alkanol (see also for example U.S. Pat. No. 3515707).

Prepolymers for units of formula (C) may be prepared by reacting N-methyl-N,N-diallyl amine with an alkyl halide such as n-octyl bromide or n-dodecyl bromide in an appropriate solvent (see for example British Pat. No. 1037028).

If monomeric bromides are initially produced, then in order to provide the quaternary ammonium compound in the most advantageous form for polymerisation, the bromide ion can be replaced by chloride ion by passage through a suitable ion-exchange resin. It is believed that polymerisation is best achieved using precursors in the form of chloride salts.

In preparing the polymers of this invention the monomers may be polymerised by a free-radical polymerisation process. In such processes the monomers may be dissolved in the desired final ratios in a polar solvent such as water, dimethylsulphoxide, dimethyl formamide, a lower alkanol, dioxane, a glycol ether or other solvent of like polarity. A free radical catalyst will be present as a polymerisation initiator. Apt catalysts include peroxides including inorganic peroxides such as hydrogen peroxide, organic peroxides, such as tertiary butyl hydroperoxide and benzoyl peroxide and peracids, such as peracetic acid. Alternatively other free radical catalysts may be employed such as azobisisobutyronitrile. The amount of catalyst used will generally be 0.5 to 5% by weight of the monomer present. A non-extreme temperature will normally be employed, for example, from 0° C. to 100° C., but a particularly suitable range is from 50° C. to 80° C., for example 70° C. The polymerisation can be carried out most conveniently at atmospheric pressure. An inert atmosphere is preferred for the polymerisation to avoid the formation of undesirable by-products. To this end the reactant mixture may be purged with nitrogen before polymerisation is initiated and a nitrogen atmosphere may aptly be maintained during the reaction.

The initial product of the polymerisation is the chloride salt of the methyl ester of the required polymer. The polymer may be de-esterified by heating in the presence of an aqueous solution of a mineral acid. Particularly preferred as a 6N solution of hydrogen chloride. The temperature of the reaction is preferably from 80° C. to 100° C. The resultant solution may be finally transformed to the required polymer by dialysing using a semi-permeable membrane. This process may be carried out over a period of 7 days. The polymer is retained within the membrane whilst the impurities in the polymer are removed through the membrane.

Suitably the reaction product of the polymerisation reaction is dialysed through a cellulose acetate membrane to remove excess ions, low molecular weight reaction products and low molecular weight polymeric reaction products. A suitable cellulose acetate membrane is a Visking membrane (available from Medicell International Ltd. London). Suitably the polymer remaining within the dialysis membrane has a molecular weight of greater than 10,000 and preferably is greater than 15,000. (Molecular weights are expressed on wt. average basis).

Alternatively the polymer may be de-esterified by allowing the polymer stand at ambient temperature, 15° to 25° C. in the presence of an aqueous solution of an alkali metal hydroxide, suitably sodium hydroxide, for sufficient time to allow de-esterification to take place. The de-esterification reaction is exothermic. Although during the course of the reaction the temperature of the reaction mixture may rise no external heating means is required. The resultant solution is neutralised with dilute mineral acid and the neutral solution dialysed using a semi-permeable membrane as described above. Suitably the dialysis will be carried out over a period of 14 days. The polymers of the invention may be isolated from the dialysed solution by freeze drying.

Preparation of N-carbomethoxymethyl-N-methyl-N,N-diallyl ammonium chloride. To a solution of diallyl methylamine (17.90 g) in acetone (35 ml) was added methyl chloracetate (17.47 g). The mixture was allowed to stand at ambient temperature for 48 hours. The solvent was then removed by evaporation under reduced pressure. The residue, a thick oil, was made more mobile by the addition of isopropanol (5.0 ml) and the product re-precipitated by the addition of ether (700 ml). The product separated as a heavy oil. The ether layer was decanted and the product again mobilised by the addition of isopropanol (5.0 ml). Any residual ether and the isopropanol were removed by evaporation under a vacuum of 1 mmHg and gentle heating. The product N-carbomethoxy methyl-N-methyl-N,N-diallyl ammonium chloride (29.20 g) was isolated as a pale yellow oil (free from starting materials by glc).

Preparation of N-carbomethoxymethyl-N-n-dodecyl-N,N-diallyl ammonium chloride. To a solution of diallyldodecylamine (26.60 g) in ethanol (50 ml) was added methyl chloracetate (16.30 g). The mixture was heated to reflux temperature and maintained at that temperature in the dark for 48 hours. The ethanol and excess methyl chloracetate were evaporated under reduced pressure to yield a viscous orange oil (38.30 g). Ethanol (0.5 ml) was added to make the oil mobile and the product was reprecipitated by 40–60 petroleum ether (400 ml). The product separated as a heavy red oil. The petroleum ether layer was decanted. The product was made more mobile with ethanol (0.5 ml) and finally any residual petroleum ether and the ethanol were removed by evaporation under a vacuum of 1 mmHg and gentle heating. The product N-carbomethoxy methyl-N-dodecyl-N,N-diallyl ammonium chloride (29.95 g) was isolated as a red oil (free of starting materials by glc).

Preparation of N-methyl-N-n-dodecyl-N,N-diallyl ammonium chloride. To a solution of diallylmethylamine (11.10 g) in isopropanol (50 ml) was added n-dodecyl bromide (24.90 g). The resultant mixture was heated in the dark under reflux for 20 hours. The cooled solution was passed down an ion-exchange column (Amberlyst A-26) in the chloride form which exchanged the bromide ion for chloride ion. The solvent was removed by evaporation under reduced pressure to give a yellow oil. The oil was then dissolved in water (130 ml) and extracted with diethyl ether (3×25 ml) to remove unchanged starting materials. The product is isolated in approximately 50% w/w solution in water by evaporating the aqueous solution to remove water (90 ml. approximately). The product N-methyl-N-n-dodecyl-N,N-diallyl ammonium chloride was obtained as a 95% yield (34.20 g) based on the dry weight of the aqueous solution.

EXAMPLE 1

Preparation of poly[N-carboxymethyl-N-methyl-N,N-diallyl]-[N-carboxymethyl-N-n-dodecyl-diallyl]-[N-methyl-N-n-dodecyl-N,N-diallyl] ammonium chloride copolymer.

To a solution of N-carbomethoxymethyl-N-methyl-N,N-diallyl ammonium chloride (5.2 g), N-carbomethoxymethyl-N-n-dodecyl-N,N-diallyl ammonium chloride (1.4 g) and a 51% aqueous solution of N-methyl-N-n-dodecyl-N,N-diallyl ammonium chloride (2.86 g, equivalent of 1.40 g dry monomer) in water (2.54 g) was added t-butyl hydroperoxide (0.28 g). The resultant solution was purged with nitrogen and maintained at 70° C. for 40 hours under nitrogen. The reaction mixture was cooled and water (150 ml) added. The resultant solution was sealed into 18/32" Visking tubing and allowed to dialyse in water (4 liters) for 7 days, replacing the water (4 liters) each day. The retentate was evaporated to dryness under reduced pressure to yield a viscous oil (4.20 g). This oil was dissolved in 6N hydrochloric acid (20 ml) and heated to 98° C. for 4 hours. The reaction mixture was cooled and water (100 ml) added. The water along with excess hydrogen chloride was removed by evaporation under reduced pressure. To the residue a further amount of water (100 ml) was added. This solution was sealed into a 18/32" Visking tubing and dialysed as previously for 3 days. The second retentate was evaporated under reduced pressure to remove water. To the solid residue was added methanol (5 ml) and isopropanol (5 ml) and the remaining traces of water in the solid removed by azeotropic distillation. The solid product was finally dried in an oven at 70° C. to give the terpolymer (2.8 g) as a yellow solid.

The proportions of starting materials are chosen such that the resultant polymer contains 65% of units of formula (A), 17.5% of units of formula (B) and 17.5% of units of formula (C) (wherein $R^1$ and $R^3$ are hydrogen atoms and $R^2$ and $R^4$ are n-unadecyl groups).

EXAMPLES 2–8

Polymers according to the present invention having compositions as given in Table 1 were made in a like manner to the polymer prepared in Example 1.

TABLE 1

| | % A | % B | $R^2$ | % C | $R^4$ |
|---|---|---|---|---|---|
| Example 2 | 55 | 20 | n-C$_{11}$H$_{23}$ | 25 | n-C$_{11}$H$_{23}$ |
| Example 3 | 62½ | 12.5 | n-C$_{11}$H$_{23}$ | 25 | n-C$_7$H$_{15}$ |
| Example 4 | 65 | 0 | | 35 | n-C$_{11}$H$_{23}$ |
| Example 5 | 65 | 7 | n-C$_{11}$H$_{23}$ | 28 | n-C$_{11}$H$_{23}$ |
| Example 6 | 70 | 0 | | 30 | n-C$_{11}$H$_{23}$ |
| Example 7 | 70 | 10 | n-C$_{11}$H$_{23}$ | 20 | n-C$_7$H$_{15}$ |
| Example 8 | 80 | 0 | | 20 | n-C$_{11}$H$_{23}$ |

In each example 1–8 units of formula (A) are derived from N-carboxymethyl-N,N-diallyl-N-methyl quaternary ammonium compound, that is where $R^1$ as defined above is a hydrogen atom. In each example 1–8 units of formula (C) are derived from N-methyl-N,N-diallyl-N-alkyl quaternary ammonium chloride, that is where $R^3$ as defined above is a hydrogen atom.

(a) Antimicrobial Test Procedure.

Antimicrobial activity was assessed using four organisms *Pseudomonas aeruginosa*, *Staphyloccocus aureus*, *Escherichi coli* and *Candida albicans*. The four organisms were inoculated separately into aqueous solutions of the test polymers at concentrations of $10^6$ organisms/ml. The concentrations of test polymers in each solution was either 0.02 ot 0.05%. Samples were withdrawn after 4 hours and were cultured in a recovery broth containing suitable inactivators. If no viable organisms were recovered the polymer had passed the test. The results are given in Table 2.

Alternatively the samples were poured into a plate and a Triptone Soy Agar solution containing suitable inactivators was added. The plates were incubated at 37° C. for 24 hours and the number of colonies counted. The number of surviving organisms/ml was then calculated. A solution of the polymer which resulted in less than 10 organisms/ml surviving from the initial challenge of $10^6$ organisms/ml had passed the test.

(b) Protein Deposition Test Procedure

Bovine serum albumin/fluorescamine to be used as the source of protein was prepared as described by Brynda et. al. in J. Biomed. Mat. Res. 1978, 12, 55. A series of polyhydroxyethyl methacrylate, (polyHEMA) contact lenses were cleaned by immersion in a 10% aqueous solution of polyoxyethylene stearate (Tween 60) subjecting the lenses and solution to ultrasonic waves for 5 minutes at 50° C. The lenses were thoroughly rinsed in distilled water to remove all traces of the surface active agent.

The cleaned lenses were then allowed to stand overnight in the presence of 5 ml. of an aqueous test solution containing 0.02% of a polymer dissolved in it. The test solution was aspirated from above the lens and the lens washed six times with distilled water, the liquid was aspirated form above the lens each time. Then the lenses were allowed to stand overnight in the presence of a 3.5 ml. of solution of 0.5 mg/ml Albumin/fluorescamine in Ringer solution. The non-bound protein was rinsed from the lens by aspirating the liquid from above the lens without allowing the coated lens to become exposed to the air. This washing and aspiration was repeated six times. Finally 4 ml. of 1% sodium dodecyl sulphate in 0.05 M borate buffer at pH 9 was added to the lens. The lens in its container was then transferred to an ultrasonic bath to remove the bound protein from the lens. The solution containing the lens was then assessed for protein content by fluorimetry at a wavelength of 390 cm$^{-1}$ for activation and 475 cm$^{-1}$ for fluorescence. The results are presented as ratio to the results obtained with a standard compound which is a terpolymer of dimethyl diallyl ammonium chloride (17.5%), N-methyl-N-n-octyl diallyl ammonium chloride (55%) and N-methyl-N-n-dodecyl diallyl ammonium chloride (27.5 g) which is known to bind protein. The results are shown in Table 2.

TABLE 2

|  | Protein Deposition (relative to standard) | Antimicrobial Effectiveness at 4 hours Concentration | |
|---|---|---|---|
|  |  | 0.02 | 0.05 |
| Example 1 | 0.40 | Pass |  |
| Example 2 | 0.66 | Pass |  |
| Example 3 | 0.42 | Pass |  |
| Example 4 | 0.78 | Pass |  |
| Example 5 | 0.48 | Pass |  |
| Example 6 | 0.65 | Pass |  |
| Example 7 | 0.42 | Pass |  |
| Example 8 | 0.69 |  | Pass |

EXAMPLE 9

Isotonic Solution of Polymer prepared in Example 1

An isotonic solution of a portion of the polymer prepared in Example 1 suitable for the sterilisation of soft contact lenses was formulated as follows:

| Polymer of Example 1 | 0.02% |
|---|---|
| Urea | 1.63% |
| Distilled water to | 100% |

The polymer and urea were taken and dissolved in water (90 ml). When all the solid had dissolved the solution was made up to 100% with distilled water.

The solution may then be sterilised by filtration through a 0.22 micron cellulose ester membrane filter and aseptically filled into sterile containers.

A portion of solution was taken and assessed for antimicrobial activity in the test described herein. No viable organisms of any of the four test organisms was recovered after four hours. Hence the solution passed the test.

EXAMPLE 10

Isotonic Solution of the Polymer prepared in Example 1.

A second isotonic solution of a portion of the polymer prepared in Example 1 which is suitable for the sterilisation of soft contact lenses was formulated as follows:
Polymer of Example 1: 0.02%
Glycerol: 2.5%
Distilled water to: 100%

The solution was prepared and tested for antimicrobial activity as described in Example 9. The solution passed the test.

EXAMPLE 11

Preparation of Poly[N-carboxymethyl-N-methyl-N,N-diallyl]-[N-carboxymethyl-N-n-dodecyl-diallyl]-[N-methyl-N-n-dodecyl-N,N-diallyl] ammonium chloride copolymer.

To a solution of N-carbomethoxymethyl-N-methyldiallyl ammonium chloride (130 g, 0.59 M) N-carbomethoxymethyl-N-n-dodecyl-N,N-diallyl ammonium chloride (35 g, 0.094 M) and N-methyl-N-n-dodecyl-N,N-diallyl ammonium chloride (35 g, 0.11 M) in water (100 ml) was added t-butyl hydroperoxide (7 g). The resultant solution was purged with nitrogen and maintained at a temperature of 70° C. for 40 hours under an atmosphere of nitrogen. The reaction mixture was cooled and then the volume of the mixture was diluted to 1000 ml by addition of water. Sodium hydroxide solution (272 ml, 10% solution) was added and the mixture allowed to stand for 1 hour. The pH of the resultant solution was adjusted to pH 7 by addition of dilute hydrochloric acid. The resultant solution wad dialyzed in 18/32" Visking tubing for 14 days. The solution retained in the Visking tubing was freeze dried to yield the polymer (86 g, 52%) as a white solid.

The proportions of starting materials are chosen such that the resultant polymer contains 65% of units of formula (A), 17.5% of units of formula (B) and 17.5% of units of formula (C) (wherein $R^1$ and $R^3$ are hydrogen atoms and $R^2$ and $R^4$ are n-unadecyl groups).

EXAMPLE 12

Isotonic solution of the Polymer prepared as in Example 11.

An isotonic solution containing polymer prepared according to the method of Example 11 which is suitable for the sterilisation of soft contact lenses was formulated as follows:
Polymer as Example 11: 0.2%
Propylene glycol: 2.0%
Distilled water to: 100.0%

The solution was prepared and tested for antimicrobial activity by the plate method described hereinbefore. The solution passed that test.

EXAMPLE 13

Isotonic solution of the Polymer prepared as in Example 11.

An isotonic solution containing polymer was prepared according to the method of Example 11 and which also contains a surface active agent was formulated as follows:
Polymer as Example 11: 0.002%
Polyoxyethylene-polyoxypropylene block copolymer (mol. wt. 2900): 0.5%
Propylene glycol: 2.0%
Distilled water to: 100.0%

The solution was prepared and tested for antimicrobial activity by the plate method described hereinbefore. The solution passed the test. This solution is suitable for use as a wetting and sterilising solution for hard and gas permeable contact lenses.

EXAMPLE 14

Isotonic solution of the Polymer prepared as in Example 11.

An isotonic solution containing polymer was prepared according to the method of Example 11 which is suitable for the sterilisation of soft contact lenses was formulated as follows:
Polymer as Example 11: 0.002%
Glycerol: 2.5%
Distilled water to: 100.0%

The solution was prepared and tested for antimicrobial activity by the plate method as described hereinbefore. The solution passed the test.

EXAMPLE 15

Isotonic solution of the Polymer prepared as in Example 1.

An isotonic solution containing polymer prepared according to the method of Example 1 which is suitable for sterilisation of soft contact lenses was formulated as follows:

Polymer as Example 1: 0.002%
Propylene glycol: 2.0%
Distilled water to: 100%

The solution was prepared and tested for antimicrobial activity by the plate method as described hereinbefore. The solution passed the test.

EXAMPLE 16

Sterilisation

A hydrophilic contact lens was placed into a closable lens case (volume 12 ml). A sterilising solution of Example 11 was introduced into the lens case which was then closed and left at ambient temperature for 6 hours. At the end of this time the lens was deemed to satisfactorily sterilised.

EXAMPLE 17

Ointment containing the Polymer as prepared in Example 1.

An ointment was formed by blending together at 80°/85° C. the following:

Liquid paraffin BP.: 20%
Cetyl alcohol: 4%
Estox 5 N: 4%
Polyoxyethylene sorbitan monostearate: 1%
Polyoxyethylene sorbitan monooleate: 1%
Propylene glycol: 7%
Polymer as Example 1: 0.2%
Water to: 100%

Demonstration of Effectiveness

The antimicrobial activity of aqueous solutions containing 0.002% of polymer prepared by the method of Example 11 made isotonic with 1.63% urea, 2.2% glycine, 2.5% glycerol and 2.0% propylene glycol were assessed using *Staphylococcus aureus* by the method described hereinbefore in the Antimicrobial Test Procedure using the plate method. The results were as follows:

| 0.002% Polymer in Aqueous Solution made isotonic with: | Survivors/ml at 4 hours. |
| --- | --- |
| 1.63% Urea | <10 |
| 2.2% Glycine | <10 |
| 2.5% Glycerol | <10 |
| 2.0% Propylene glycol | <10 |

The antimicrobial activity of aqueous solution containing 0.002% of polymer prepared by the method of Example 11 made isotonic with 2.5% glycerol was assessed using various organisms by the plate method as described hereinbefore. The results were as follows:

| Organism | Survivors/ml at 4 hours. |
| --- | --- |
| *Staphylococcus aureus* NCTC 6571 | <10 |
| *Pseudomonas aeruginosa* NCTC 6750 | <10 |
| Klebsiella species | <10 |
| Proteus species | <10 |
| Enterobacta species | <10 |
| *Candida albicans* LSH 3153 | <10 |

The antimicrobial activity of an aqueous solution containing 0.002% of polymer prepared by the method of Example 11 made isotonic with 2.5% glycerol and containing in addition 0.5% polyoxyethylene-polyoxyporpylene diol block copolymer (molecular weight 2900) was assessed using *Staphylococcus aureus* and *Candida albicans* by the plate method described hereinbefore. The results were as follows:

| Organism | Survivors/ml at 4 hours |
| --- | --- |
| *Staphylococcus aureus* NCTC 6571 | <10 |
| *Candida albicans* LSH 3153 | <10 |

What we claim is:

1. A polymer consisting essentially of 55 to 90% by weight of the formula (A):

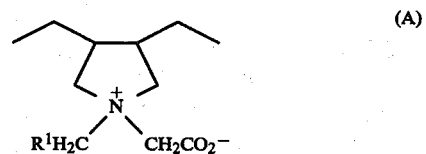

wherein $R^1$ is a hydrogen atom or an alkyl group of 1 to 3 carbon atoms; 10 to 45% of units of the formulae (B) and (C): up to 22% by weight of units of formula (B):

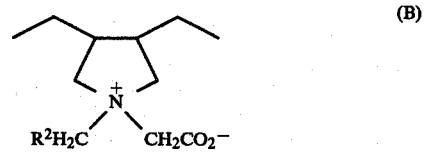

and 10 to 35% by weight of units of formula (C):

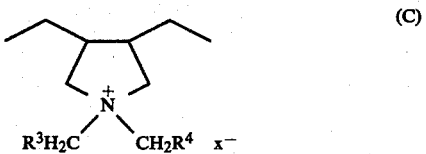

wherein $R^2$ is a hydrocarbon group of 5 to 19 carbon atoms, $R^3$ is a hydrogen atom or an alkyl group of 1 to 3 carbon atoms, $R^4$ is a hydrocarbon group of 5 to 19 carbon atoms and $X^-$ is an anion.

2. A polymer as claimed in claim 1 wherein $R^1$ and $R^3$ are hydrogen atoms and $R^2$ and $R^4$ are n-alkyl groups containing from 7 to 13 carbon atoms.

3. A polymer as claimed in claim 2 in which $R^2$ and $R^4$ are n-alkyl groups which contain 11 carbon atoms.

4. A polymer as claimed in claim 2 in which $X^-$ is a chloride ion.

5. A polymer as claimed in claim 2 which contains 60 to 80% of units of the formula (A), up to 22% of units of the formula (B) and 10 to 35% of units of the formula (C).

6. A polymer as claimed in claim 2, from which low molecular weight material has been removed by dialysis of an aqueous solution of the polymer using a semipermeable membrane capable of allowing transfer of such low molecular weight material.

7. A polymer consisting essentially of 62 to 70% by weight of units of the formula (A):

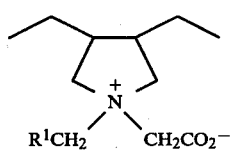 (A)

wherein $R^1$ is a hydrogen atom or an alkyl group of 1 to 3 carbon atoms; 15 to 20% by weight of units of the formula B:

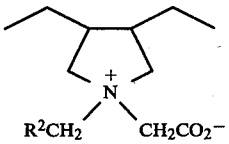

wherein $R^2$ is a hydrocarbon group of 5 to 19 carbon atoms; and 15 to 30% by weight of units of the formula C:

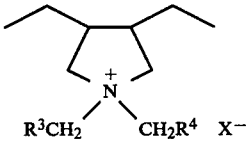 (C)

wherein $R^3$ is a hydrogen atom or an alkyl group of 1 to 3 carbon atoms, $R^4$ is a hydrocarbon group of 5 to 19 carbon atoms and $X^-$ is an anion.

8. A polymer consisting essentially of 65% by weight of units of the formula:

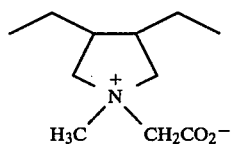

17.5% by weight of units of the formula

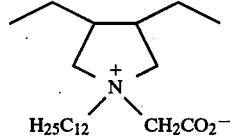

and 17.5% by weight of units of the formula

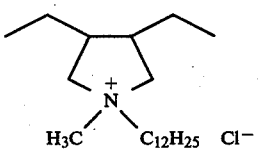

* * * * *